United States Patent [19]

Parslow et al.

[11] Patent Number: 4,889,802

[45] Date of Patent: Dec. 26, 1989

[54] ENHANCED PRODUCTION OF RECOMBINANT PROTEINS IN MYELOMA CELLS

[75] Inventors: Tristram G. Parslow; Keith R. Yamamoto, both of San Francisco, Calif.

[73] Assignee: The Regents of the University of California, Oakland, Calif.

[21] Appl. No.: 911,259

[22] Filed: Sep. 24, 1986

[51] Int. Cl.$^4$ .................. C12P 21/00; C12N 15/00
[52] U.S. Cl. ................... 435/69.1; 435/172.3; 435/240.2; 435/320; 435/69.4; 435/69.5; 435/69.51; 435/69.52; 435/69.6; 935/23; 935/32; 935/33; 935/70; 935/89; 935/106
[58] Field of Search .................. 435/68, 70, 255, 320, 435/241, 172.3, 317, 240.2; 935/21, 26, 23, 32, 24, 33, 34, 36

[56] References Cited

U.S. PATENT DOCUMENTS 4,663,281   5/1987   Gillies et al. ................. 435/68

OTHER PUBLICATIONS

Sen et al., Cell, vol. 46, 705–716, Aug. 1986.
Karin et al., Cell, vol. 36, 371–379, Feb. 1984.
Singh et al., Nature, vol. 319, 1986 pp. 154–158.

Primary Examiner—Thomas G. Wiseman
Assistant Examiner—Patrica Carson
Attorney, Agent, or Firm—Irell & Manella

[57] ABSTRACT

A mammalian myeloma cell comprising a double-stranded DNA molecule in its genome containing a coding sequence encoding a non-immunoglobulin protein, a non-immunoglobulin promoter sequence adjacent to the 5' terminus of said coding sequence, and the 8-base pair nucleotide sequence 5'-ATTTGCAT-3' located 5' to the transcription initiation site of said promoter sequence. The DNA molecule may optionally contain an enhancer element. Methods of producing non-immunoglobulin protein and DNA molecules are also provided.

28 Claims, 1 Drawing Sheet

ENHANCED PRODUCTION OF RECOMBINANT PROTEINS IN MYELOMA CELLS

GOVERNMENT GRANT

This invention was made with U.S. Government support under Grant Nos. AI-22536 and CA-20535 with the National Institutes of Health and the University of California. The U.S. Government has certain rights in this invention.

TECHNICAL FIELD

The present invention relates to the expression of recombinant proteins. More particularly, the present venture relates to enhanced expression levels of recombinant proteins in myeloma cells.

BACKGROUND

Expressing recombinant genes encoding mammalian proteins in bacteria or yeast has not always been successful. First, these expression systems have not always properly processed the polypeptide into mature protein. Second, some mammalian genes simply have not been successfully expressed in these systems, probably because of codon choices that are incompatible with cellular RNases. It is preferred in many cases, therefore, to express genes for mammalian proteins in a mammalian expression system.

Many mammalian genes are expressed under the control of a tissue-specific promoter. Thus, it would be necessary to express genomic clones of these genes in the appropriate primary tissue. Unfortunately, most mammalian primary tissue does not grow well in culture. An exception to that is malignant B-lymphocytes (myelomas). These cells also produce immunoglobulins at very high levels. Only limited success has been achieved, however, in expressing non-immunoglobulin genes under the control of their own promoters in myelomas. Banerji et al. (1983) Cell 33: 729-740, discloses the expression of rabbit β-globin gene under the control of a mouse immunoglobulin heavy chain enhancer in myeloma cells. Rice et al. (1983) Proc. Nat'l. Acad. Sci. USA 79: 7862-7865, discloses the production of a murine lymphoid cell line which expresses a foreign immunoglobulin gene and a bacterial marker gene. See also Oi et al. (1983), Proc. Nat'l. Acad. Sci. 80: 825-829.

Transcription enhancer elements are DNA sequences that can act over distances of several kilobases to increase the activity of a promoter in cis, regardless of orientation relative to the promoter. Both heavy and light chain immunoglobulin genes have enhancers. Several reports have appeared in the literature describing the sequence, location, and function of the immunoglobulin κ light chain transcription enhancer element. See Emorine et al. (1983) Nature 304: 447-449; Parslow et al. (1983) Nucleic Acids Res. 11: 4775-4792; Picard et al. (1984) Nature 307: 80-82; Parslow et al. (1982) Nature 299: 449-451; Queen et al. (1983) Cell 33: 741-748; Bergman et al. (1984) Proc. Nat'l. Acad. Sci. USA 81: 7041-7045. The following articles also relate to transcription enhancement elements: Scholer et al. (1986) Science 232: 76-80; Banerji et al. (1981) Cell 27: 299-308; Moreau et al. (1981) Nucleic Acid. Res. 9: 6251; Gruss et al. (1981) Proc. Nat'l. Acad. Sci. USA 78: 943-947; Fromm et al. (1982) J. Mol. Appl. Genet. 1: 457; Gruss et al. (1983) Cell 33: 313; Gillies et al. (1983) Cell 33: 717-728; Neuberger (1983) Embo. J. 2: 1373-1378; Walker et al. (1983) Nature 306: 557-561; Haslinger et al. (1985) Proc. Nat'l. Acad. Sci. USA 82: 8572; Mercola et al. (1984) Science 227: 266-270; Weiher et al. (1983) Science 219: 626-631.

In Parslow et al. (1984) Proc. Nat'l Acad. Sci. USA 81: 2650-2654, and Falkner et al. (1984) Nature 310: 71-74, short nucleotide sequences (an octamer and a decamer, respectively) were reported to be essential elements of the immunoglobulin heavy chain and light chain promoters. The sequences occur, however, in opposite orientations in the two immunoglobulin genes. Parslow et al. (1984) also reported the occurrence of the octamer in HLA-DR genes.

Mason et al. (1985) Cell 41: 479-487, discloses the transformation of myelomas with a human β-globin gene, including the coding sequence and the TATA box, ligated to immunoglobulin heavy chain promoter sequences. The hybrid construction was found to be nonfunctional without the octamer in the heavy chain orientation.

Mattaj et al. (1985) Nature 316: 163-167, discloses that the above octamer sequence occurs in the 5' region of Xenopus U2 gene, and that deletion of the octamer decreases promoter activity 10-20 fold. The octamer occurs in the heavy chain orientation.

Additional articles discussing the octamer include Bergman et al. (1984), supra; Singh et al. (1986) Nature 319: 154-158.

SUMMARY OF THE INVENTION

It has now been discovered that a particular octanucleotide sequence found in the promoter region of immunoglobulin genes can increase the rate of transcription of genes under the control of non-immunoglobulin promoters in, inter alia, myeloma cells. Furthermore, it has been discovered that the transcription rate is increased even further when this octanucleotide is employed in conjunction with a transcription enhancer element. Thus, the present invention allows for the expression of foreign genes in myeloma cell lines at high levels, even though they are not under the control of an immunoglobulin promoter.

In one embodiment, the present invention is directed to a mammalian myeloma cell, the genome of which comprises a double-stranded DNA molecule containing: (i) a coding sequence encoding a non-immunoglobulin protein and bounded by a translation start codon at its 5' terminus and a translation stop codon on its 3' terminus; (ii) a non-immunoglobulin promoter sequence adjacent to the 5' terminus of said coding sequence, said promoter sequence containing a transcription initiation site and capable of initiating transcription of said coding sequence in a mammalian myeloma cell; and (iii) the 8-base pair nucleotide sequence 5'-ATTTGCAT-3' on the nontranscribed strand located 5' to said transcription initiation site and in a position whereby the rate of transcription of said coding sequence in said mammalian myeloma cell is increased.

The present invention is also directed to the myeloma cells described above wherein said double-stranded DNA molecule also contains a transcription enhancer element located so as to increase the rate of transcription of said coding sequence in a mammalian myeloma cell.

In another embodiment, the present invention is directed to a method of producing non-immunoglobulin proteins comprising: (a) providing a clone of the above myeloma cells; (b) growing said clone under conditions whereby said non-immunoglobulin protein is expressed; and (c) recovering said non-immunoglobulin protein.

In yet another embodiment, the present invention is directed to DNA molecules that can be used to transform myeloma cells.

These and other embodiments of the present invention will be readily apparent to those of ordinary skill in the art from the following description.

DETAILED DESCRIPTION

Figure 1:
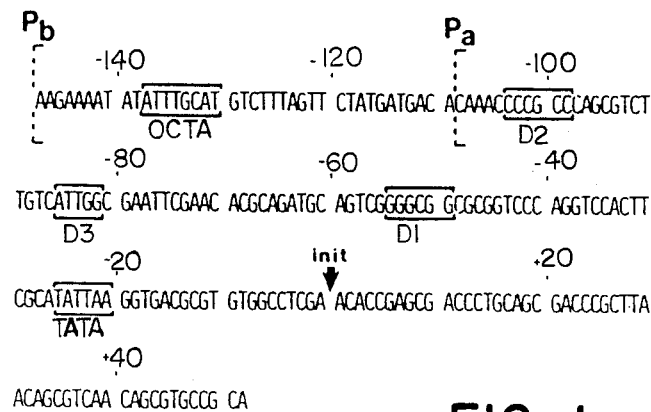
FIG. 1 shows the nucleotide sequence of the nontranscribed strand of the wild-type thymidine kinase promoter of the herpes simplex virus.

The practice of the present invention will employ, unless otherwise indicated, conventional molecular biology, microbiology, and recombinant DNA techniques within the skill of the art. Such techniques are explained fully in the literature. See e.g., Maniatis, Fritsch & Sambrook, MOLECULAR CLONING: A LABORATORY MANUAL (1982); DNA CLONING, Volumes I and II (D. N. Glover ed. 1985); OLIGONUCLEOTIDE SYNTHESIS (M. J. Gait ed. 1984); NUCLEIC ACID HYBRIDIZATION (B. D. Hames & S. J. Higgins eds. 1985); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986).

In describing the present invention, the following terminology will be used in accordance with the definitions set out below.

A "replicon" is any genetic element (e.g., plasmid, chromosome, virus) that behaves as an autonomous unit of DNA replication in vivo; i.e., capable of replication under its own control.

A "vector" is a replicon, such as plasmid or cosmid, to which another DNA segment may be attached so as to bring about the replication of the attached segment.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules, viruses, plasmids, and chromosomes. In discussing the structure of particular double-stranded DNA molecules, sequences will be described herein according to the normal convention of giving only the sequence in the 5' to 3' direction along the nontranscribed (anti-sense) strand of DNA (i.e., the strand having a sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eukaryotic mRNA, genomic DNA sequences from eukaryotic (e.g., mammalian) DNA, and even synthetic DNA sequences. A polyadenylation signal will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the translation start codon of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains responsible for the binding of RNA polymerase. Eukaryotic promoters will often, but not always, contain "TATA" boxes and "CAT" boxes. A "non-immunoglobulin" promoter is a promoter whose sequence is not homologous to a promoter sequence, as defined above, found in a mammalian immunoglobulin gene.

"Transcription enhancer elements" are DNA sequences, as understood in the art, that significantly increases the transcription rate of a gene in cis independent of the enhancer's orientation, and (to a large extent) location with respect to the gene. They are believed to be binding sites for trans-acting regulatory proteins. Many said sequences are known in the art. See, e.g., Scholer et al. (1986) Science 232: 76–80 and papers cited therein; Background section, supra.

A cell which has been "transformed" by an exogenous DNA sequence is a cell which has had the exogenous DNA introduced into it. The exogenous DNA may or may not be integrated (covalently linked) to chromosomal DNA making up the genome of the cell. "Stably" integrated genes are those which are inherited through chromosome replication by daughter cells. This stability is exhibited by the ability to establish cell lines or clones comprised of a population containing the exogenous DNA. A "clone" or "cell line" is a population of cells derived from a single cell or common ancestor by mitosis and is capable of stable growth in vitro for many generations.

"Myeloma" cells are malignant cells of B-lymphocyte lineage and include, as used herein, primary tumor cells, cells from established myeloma cell lines, and hybrid cells produced from myeloma cells that retain the characteristic growth properties of myeloma cells.

Two DNA sequences are "substantially homologous" when at least about 90%, and preferably at least about 95%, of the nucleotides match over the defined length of the DNA sequences. Sequences that are substantially homologous can be identified in a Southern hybridization experiment under, for example, stringent conditions. See, e.g., Maniatis et al., supra; DNA CLONING, supra.

In the practice of the present invention, an expression cassette is constructed containing a desired coding sequence under the control of a non-immunoglobulin promoter sequence and the octamer 5'-ATTTGCAT-3' (hereinafter referred to as the "OCTA" sequence). Thus, the completed expression cassette comprises, in the 5' to 3' direction, the OCTA sequence, the non-immunoglobulin promoter sequence, and the coding sequence. In a preferred embodiment of this invention, the expression cassette also contains a transcription enhancer element located at a position which increases the rate of transcription of the coding sequence in a mammalian myeloma cell.

Preferred coding sequences include those encoding enzymes, hormones, lymphokines and cellular growth factors. Examples of such proteins whose genes have been cloned include plasminogen activator, blood clotting factors, growth hormone, luteinizing hormone, insulin, interleuken-1, interleuken-2, alpha-interferon. β-interferon, γ-interferon, tumor necrosis factor, and colony stimulating factor. The coding sequence may also be a "marker" gene, which is used to cotransform a myeloma cell, particularly when the second coding sequence is for a mammalian protein that is not easily detected in an in vitro assay used to screen potential transformants. The marker coding sequence can encode a protein which allows transformed myeloma cells to survive in a selection step which kills myeloma cells not containing the marker sequence. Well known marker genes are known in the art, including, but not limited to, the gene for chloramphenicol acetyltransferase (CAT), neomycin phosphotransferase ($neo^R$), hypoxanthine phosphoribosyltransferase (hpt), and thymidine kinase (tk). Cells transformed with coding sequences encoding these proteins are able to survive on media which would otherwise be toxic to the cell. Other types of markers, such as β-galactosidase (lacZ), cause cells transformed therewith to change color under certain conditions, thus allowing their selection.

The non-immunoglobulin promoter sequence is located upstream (adjacent to the 5' terminus) of the selected coding sequence so as to place the coding sequence under the control of the promoter sequence (i.e., the promoter sequence initiates transcription of the coding sequence in vivo). The promoter sequence is one that can function in a myeloma cell, although not necessarily at significant levels in absence of the OCTA sequence and/or enhancer sequence. Furthermore, it may or may not be heterologous to the coding sequence. For example, if the coding sequence is a genomic clone of a mammalian protein, it may be desirable to leave that coding sequence under the control of its own promoter, providing that promoter is functional (with the addition of the OCTA if the clone does not already contain the OCTA in the upstream region) in a myeloma cell. On the other hand, it may be desirable to place mammalian protein coding sequences under the control of a heterologous non-immunoglobulin promoter. It will also, of course, be necessary to place coding sequences from bacteria (e.g., selectable markers) under the control of an appropriate eukaryotic promoter. Numerous eukaryotic promoters suitable for use in chimeric constructions are known in the art, including, but not limited to, the thymidine kinase promoter of the herpes simplex virus, a β-globin promoter (e.g., rabbit), and the adenovirus major late promoter. The selection of the appropriate promoter sequence is within the skill of the art.

A key feature of the present invention is that the promoter and coding sequence are placed under the control of the OCTA, which is located 5' to the transcription initiation site of the promoter. This can be accomplished, for example, by selecting a non-immunoglobulin promoter which already possesses the OCTA in the 5' region (e.g., herpes simplex tk promoter), or ligating the OCTA to the 5' terminus of a desired promoter. The latter approach may be desirable, for example, to combine the high levels of expression possible from the OCTA sequence with the ability to regulate an inducible non-immunoglobulin promoter that does not contain the OCTA sequence. As indicated above, the OCTA sequence occurs in both heavy chain and light chain immunoglobulin genes in nature, but, in opposite orientations. It has been found that in using this sequence to enhance the expression of non-immunoglobulins, it is essential to employ the OCTA in the light-chain orientation with respect to the coding sequence. If the opposite orientation is employed, transcription levels are not enhanced. In the light-chain orientation, the nucleotide sequence on the nontranscribed (antisense) DNA strand in the OCTA region is 5'-ATTTGCAT-3'. The location of the octamer does not appear to be critical, provided it is in the light-chain orientation and located upstream from the transcription initiation site of the promoter sequence. The determination of the optimum spacing from the transcription initiation site is within the skill of the art. Generally, the octamer will be located within 500 base pairs of the transcription initiation site, and usually within about 50 to about 200 base pairs.

In a preferred embodiment of the present invention, the transcription of the coding sequence is also under control of a transcription enhancer element. Many such enhancers are known in the art. See e.g., Picard et al. (1984) Nature: 307: 80–82; de Villieris et al. (1981) Nucleic Acids Res. 9: 6251–6264; Banerji et al. (1981) Cell 27: 299–308; Moreau et al. (1981) Nucleic Acids Res. 9: 6047–6068; Banerji et al. (1983) Cell 33: 729–740; Gillies et al. (1983) Cell 33: 717–728; Neuberger (1983) Embo J. 2: 1373–1378. Known enhancers include, but are not limited to, the SV40 enhancer, the murine immunoglobulin heavy-chain enhancer, the murine immunoglobulin k light-chain enhancer, Moloney murine-sarcoma viral enhancer and the polyoma virus enhancer. The preferred enhancers are mammalian immunoglobulin enhancers, particularly light chain enhancers such as the κ enhancer.

The location of the enhancer element with respect to the coding sequence or promoter sequence is not critical. This aspect of enhancer location is, in fact, one of the primary defining features of enhancer elements. They generally are functional in any orientation within several thousand base pairs of the promoter. They may be located either 5' or 3' to the gene, or even within the gene itself (e.g., within an intron). Thus, there will be a multitude of suitable locations for the enhancer with respect to the other elements of the expression cassette. One of ordinary skill in the art, therefore, will have no difficulty in placing the enhancer element within the expression cassette so that the transcription of the coding sequence will be increased in a myeloma cell. For ease of construction, however, one can simply locate the enhancer element several hundred or a thousand base pairs upstream 5' from the OCTA sequence.

It is generally preferred to clone the elements of the expression cassette, as well as the completed expression cassette, in a suitable vector. For example, many E. coli plasmid vectors suitable for use in the construction and cloning of the expression cassette are well-known in the art. The selection of such vectors is not critical and is within the skill of the art.

Mammalian myeloma cells are transformed with the expression cassettes described above. The method of transforming myeloma cells in the practice of the present invention is not critical. The selection of an appropriate method is within the skill of the art. Many methods of transforming mammalian cells are known in the art. For example, viral transformation vectors are known, including vectors based on SV40, papillomavirus, adenovirus, and retroviruses. See, e.g., Subramani et al. (1983) Anal. Biochem. 135: 1; Rigby (1983) J. Gen. Virol. 64: 2055; Rigby in GENETIC ENGINEERING Vol. III, p. 83 (R. Williamson ed. 1982); DNA CLONING, Vol. II, pp. 191–239 (D. Glover ed. 1985). Other methods of transforming mammalian cells, such as DEAE-dextran, involve the direct uptake of DNA independent of a mammalian transformation vector. See e.g., DNA CLONING, Vol. II, supra, pp. 143–190; Somparyarc et al (1981) Proc. Nat'l. Acad. Sci. USA 12: 7575. A widely used method of transforming mammalian cells is the calcium phosphate method. See, e.g., DNA CLONING Vol. II, supra, pp. 152–154; Graham et al. (1973) Virology 52: 456.

When a transformation vector is employed, the expression cassette of the present invention can be cloned directly into the transformation vector. When a DNA-uptake transformation method is employed (i.e., DEAE-dextran or calcium phosphate) cloning vectors or linear DNA molecules containing the expression cassette can be used in the transformation protocol without transfering the constructions. If there is no convenient assay for detecting transformants containing a selected coding sequence, it may be desirable to "co-transform" the mammalian myeloma cell with the expression cassette and a second DNA segment carrying a marker gene. See e.g. U.S. Pat. No. 4,399,216; Lowry et al. (1980) Cell 22: 817. The marker gene may or may not be constructed according to the above-described expression cassette.

After carrying out the chosen transformation protocol, myeloma cells are assayed for the presence of the expression cassette and/or marker gene. In the preferred embodiment, the presence of the selected coding sequence in the expression cassette (or a separate marker gene co-transformed with the expression cassette) is determined by a convenient assay. Transformed cells are then passaged for a sufficient period of time (preferably under selective pressure) to ensure that the expression cassette is stably incorporated into the genome of the cell, and not simply expressed transiently or extrachromosomally. The determination of the appropriate number of passages is within the skill of the art. Once transformed myeloma cells have demonstrated stability over several generations, individual cells can be clonally expanded into cell lines by known techniques. These cell lines will comprise substantially pure cultures of clones of myeloma cells containing the expression cassette incorporated into the genome.

The protein encoded by the coding sequence of the expression cassette is produced by growing myeloma cells transformed by the expression cassettes of the present invention under the appropriate conditions so that the protein is expressed. If the promoter is inducible, it will be necessary to grow the cells under conditions that provide the proper stimulus to the promoter. Methods for growing hybridoma cells for monoclonal antibody production can be readily applied to transformed myeloma cells according the present invention, and thereby producing the desired non-immunoglobulin protein. Immobilized, serum-free cell culture systems are preferred methods of producing the proteins encoded by the expression cassettes. Expression cassette-transformed cell lines of the present invention, however, can also be grown in mouse ascites, provided the mouse is not adversely affected by any secreted protein.

The non-immunoglobulin protein produced according to the present invention is recovered and purified employing conventional techniques known to those of skill in the art. For example, if the coding sequence contains a leader sequence which permits the transport of the encoded protein through the cell wall of the myeloma, the encoded protein will be secreted and can be recovered from growth medium employing conventional techniques. If the protein is not secreted, however, it will be necessary to harvest and lyse the cells to recover the protein. The recovery and purification techniques will depend on the nature of the non-immunoglobulin protein encoded by the expression cassette. The selection of the appropriate techniques, however, is within the skill of the art.

EXAMPLES

Set forth below are specific embodiments of the present invention. These examples are included for illustrative purposes only and are not intended to limit the scope of the present invention in any way. Many standard techniques are employed in the examples, and one of ordinary skill in the art will be able to substitute alternative and/or equivalent techniques therefor. Thus, variations on the embodiment set forth below are intended to be within the scope of the invention.

I.

The following example describes the construction of expression cassettes according to the present invention.

FIG. 1 shows the structure of the herpes simplex tk promoter. The sequence shown extends from position +55 to −148. The transcription initiation site (init), the TATA box and three putative protein binding regions (D1, D2, & D3) are shown in the sequence extending to position −109 ($P_a$). This portion has previously been rigorously defined as containing the sequence elements required for full activity of the promoter. See, e.g., McKnight et al. (1982) Science 217: 316–324; El Kareh et al. (1985) Proc. Nat'l Acad. Sci. USA 82: 1002–1006; Eisenberg et al. (1985) Molec. Cell. Biol. 5: 1940–1947; Jones et al. (1985) Cell 42: 559–572. Upstream from the central region, between residues −131 and −138, is a perfect copy of the kappa light chain octanucleotide (OCTA). The octanucleotide is contained in the segment extending to −148 ($P_b$). The segment $P_a$ is referred to hereinafter as promoter A and segment $P_b$ is hereinafter referred to as promoter B.

Figure 2:
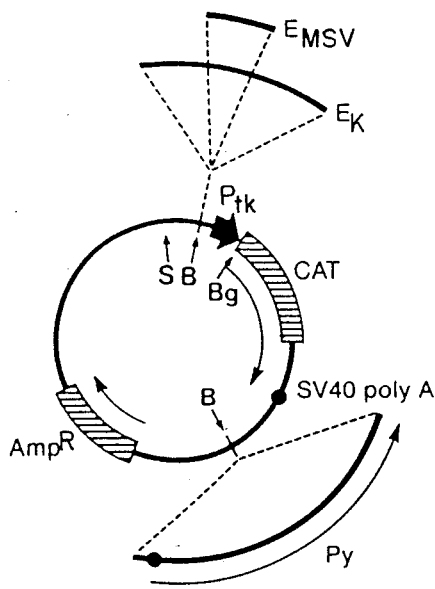
FIG. 2 is a restriction map of plasmid vectors containing expression cassettes of the present invention. The restriction sites in the figure are indicated as follows: B=BamHI, Bg=BglII, and S=SalI.

FIG. 2 shows the general structure of plasmids containing expression cassettes according to the present invention. For ease of measurement of promoter activity, the bacterial chloramphenicol acetyl transferase (CAT) gene, a selectable marker was chosen as the coding sequence in expression cassettes according to the present invention. See, Gorman et al. (1982) Molec. Cell. Biol. 2: 1044–1051. The plasmids were constructed from the 4.4 kb plasmid pCAT3M which contains a promoterless CAT gene, a polylinker upstream from the CAT gene, and the SV40 polyadenylation signal downstream from the gene. See, Laimins et al. (1984) J. Virol. 49: 183–189. An XbaI site within the polylinker of pCAT3M was blunted with DNA polymerase I and replaced by a SalI linker to produce pCAT3MS. A 3.6 kb segment (Py) carrying the origin and early region of the polyoma virus was inserted into the downstream BamHI site of pCAT3MS to give pCAT3MSP. See Queen et al. (1983) Cell 33: 741-748. Promoter fragments were inserted between the SalI and BglII sites of either pCAT3MS or pCAT3MSP after ligating the 275 base pair SalI/BamHI fragment of pBR322 to the upstream (BamHI) and of each promoter fragment. In some cases, enhancer sequences were ligated into the BamHI site immediately upstream from the promoter. The murine immunoglobulin kappa light chain enhancer ($E_K$) is contained within a 1.3 kb HindIII/HpaI fragment spanning the 3' half of the large kappa intron. See Picard et al. (1984) Nature 307: 80–82. This fragment was modified by the addition of BglII linkers. The enhancer for the Moloney murine sarcoma virus ($E_{MSV}$) is contained in a 0.35 kb BamHI fragment of the viral genome. See De Franco et al. (1986) Molec. Cell. Biol. 6: 993-1001. The enhancers and polyoma sequences were used in inverted orientation only.

Figure 3:
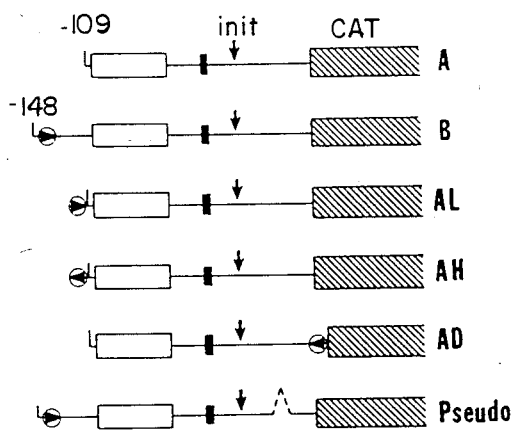
FIG. 3 is a schematic representation of promoter constructs, including expression cassettes according to the present invention, tested for enhanced expression.

A series of recombinant plasmids according to FIG. 2 were constructed containing various expression cassettes. In most instances, promoter constructs were inserted into pCAT3MSP (containing the polyoma sequence). The selection of pCAT3MS or pCAT3MSP, however, did not affect the results obtained in Example II. Some of the promoter constructs tested are shown in FIG. 3. The TATA box is shown as the closed rectangle, the region containing the distal elements D1-D3 is shown as an open rectangle, and the OCTA sequence is shown as a circle with its orientation indicated by the arrow within the circle. Construct A employs promoter A (segment $P_a$) as the promoter sequence in the plasmid. Construct B was made by cloning promoter B (segment $P_b$) into the plasmid. A double-stranded synthetic oligonucleotide, whose sequence (TATTTGCATGCA) includes the OCTA sequence, was modified by the addition of BglII-complimentary ends and then ligated into the BamHI site at the 5' end of construct A. Insertion of this element in the light chain orientation gave construct AL, while insertion in the heavy chain orientation gave construct AH. Construct AD was produced by inserting the same double-stranded sequence in the heavy chain orientation into the BglII site at ×55. The pseudo wild-type construct (PSEUDO) contains a derivative of promoter B in which residues +16 through +36 have been deleted and replaced by a 10 base pair BamHI linker. The OCTA sequence lies at position −138 in the pseudo construct (as well as in promoter B).

The expression cassettes described above were constructed employing standard recombinant DNA techniques. As indicated in Example II, constructs according to the present invention (i.e., constructs B, AL, and PSEUDO) exhibited enhanced transcription of the CAT coding sequence in mammalian myeloma cells.

II.

This example describes the production of transformed myeloma cells containing expression cassettes described in Example I.

Plasmids containing expression cassettes described in Example I were used to transfect mouse myeloma cell lines P3X63Ag8 and SP2/0. Transfection was performed by the method of Banerji et al. (1983) Cell 33: 729-740. Briefly, this method involves taking cultures of 10-20% confluency in 100 mm plates and rinsing them in Tris-buffered saline (TBS), exposing them to 1 μg plasmid DNA in 0.6 ml of TBS containing 0.5 mg/ml DEAE-dextran for 30 minutes at room temperature. The cells are then treated with 0.1 mM chloroquine in growth medium at 37° C. for 3.5 hours. Mouse 3T3 fibroblast cells were also transfected, but the calcium phosphate method was employed as described in DeFranco et al. (1986) Molec. Cell. Biol. 6: 993-1001.

The strength of the various promoter constructs in the expression cassettes were tested in a CAT enzyme assay performed essentially as described in Gorman et al. (1982) Molec. Cell. Biol. 2: 1044-1051, and quantified by scintillation counting. The cells transfected with various constructs had CAT activity assayed 48 hours (myeloma cells) or 12 hours (fibroblasts) after transfection.

The results are shown in Table I. All of the data in the table is corrected for trace levels of CAT activity present in untransfected cells. CAT activities were normalized to one construct for each cell line and do not reflect the relative activities between cell lines. Values given represent the mean of 2 to 9 determinations of a given cell line, ±SEM. In most cases, more than one preparation of each plasmid was tested. Data shown for myeloma cells are a composite of results from 2 different cell lines using vectors that either contained or lacked polyoma viral sequences. The presence of these sequences had no systematic qualitative affect upon the results obtained. ,0210

As shown in the table, plasmids containing promoter A yielded a relatively low basal level of enzyme expression, whereas those containing promoter B produced approximately 3- to 4-fold higher levels of CAT activity ($p<0.01$). Promoter AL, which contains the synthetic octanucleotide immediately upstream from promoter A also showed expression levels equivalent to that of promoter B. When the kappa enhancer was inserted 0.6 kb upstream from promoter A, there was a 3- to 5-fold increase in CAT expression above basal level. Fusion of the kappa enhancer with promoter B, however, yielded an averaged 15-fold increase of CAT expression over basal value. A similar (11-fold) increase was achieved with a combination of the kappa enhancer and promoter AL. Results obtained were essentially identical for both myeloma cell lines tested.

The CAT assay results were confirmed and extended by transcript analysis using a primer extension assay. RNA was isolated from transformed P3X63Ag8 myeloma cells 48 hours after transfection as described in Parslow et al. (1983) Science 220: 1389-1391. A $^{32}P$ end-labelled synthetic DNA primer complimentary to sequences 5 to 31 base pairs upstream from the CAT initiation codon was annealed to 25 μg of RNA and subjected to primer extension. An autoradiogram of the elongation products after fractionation by gel electrophoresis shows that the vast majority of transcripts initiated within a 4 bp region spanning residues −1 through +3, a pattern of initiation that is characteristic of the tk promoter in a variety of cell types and in cell-free transcription. Thus, all of the promoter constructs directed accurate transcriptional initiation. In addition, the relative abundance of correctly-initiated transcripts, as determined by scintillation counting, paralleled closely the observed differences in CAT enzyme activity. Promoters containing both the octanucleotide and the light chain orientation and the kappa enhancer exceeded basal level promoter activity by more than an order of magnitude. It was also found, however, that the octanucleotide had no effect when placed in the inverted, heavy chain orientation immediately upstream of promoter A (promoter AH). The octanucleotide also proved to be inactive when inserted 55 bp downstream from the initiation site (promoter AD).

III.

Myeloma cells transformed by the expression cassettes of the present invention, as described in Example II above, are passage for a sufficient period in culture to produce stable transformants. See, e.g., Gopal (1985) Molec. Cell. Biol. 5: 1188. Cell lines containing promoter constructs B or AL and the kappa enhancer can then be grown under standard conditions known in the art for culturing myeloma cells. Such growing cell lines produce the CAT enzyme at high levels. The enzyme can be recovered from growing cultures using standard techniques.

Variations of the above specific embodiments, particularly in the choice of coding sequence, are readily within the skill of the ordinary artisan and do not depart from the scope of the present invention as described in the following claims.

We claim:

1. A mammalian myeloma cell, the genome of which comprises a double-stranded DNA molecule containing:
   (i) a coding sequence encoding a non-immunoglobulin protein and bounded by a translation start codon at its 5' terminus and a translation stop codon on its 3' terminus;
   (ii) a non-immunoglobulin promoter sequence adjacent to the 5' terminus of said coding sequence, said promoter sequence containing a transcription initiation site and capable of initiating transcription of said coding sequence in a mammalian myeloma cell; and
   (iii) the 8-base pair nucleotide sequence 5'-ATTTGCAT-3' on the nontranscribed strand located 5' to said transcription initiation site and in a position whereby the rate of transcription of said coding sequence in said mammalian myeloma cell is increased.

2. The myeloma cell line of claim 1 wherein said double-stranded DNA molecule also contains a mammalian kappa light-chain immunoglobulin gene transcription enhancer element located so as to increase the rate of transcription of said coding sequence in said mammalian myeloma cell.

3. The myeloma cell of claim 2 wherein said enhancer is a murine enhancer.

4. The myeloma cell of claim 1 wherein said protein is a mammalian protein.

5. The myeloma cell of claim 2 wherein said protein is a mammalian protein.

6. The myeloma cell of claim 3 wherein said protein is a mammalian protein.

7. The myeloma cell of claim 6 wherein said 8-base pair sequence is located from about 50 to about 500 base pairs from said transcription initiation site.

8. The myeloma cell of claim 7 wherein said 8-base pair sequence is located from about 50 to about 200 base pairs from said transcription initiation site.

9. The myeloma cell of claim 6 wherein said transcription enhancer element is located 5' to said 8-base pair sequence.

10. The myeloma cell of claim 7 wherein said transcription enhancer element is located 5' to said 8-base pair sequence.

11. The myeloma cell of claim 8 wherein said transcription enhancer element is located 5' to said 8-base pair sequence.

12. A murine myeloma cell according to claim 3 wherein said protein is a mammalian protein, and said 8-base pair sequence is located from about 50 to about 200 base pairs from said transcription initiation site.

13. The myeloma cell of claim 12 wherein said promoter sequence is substantially homologous to the wild-type thymidine kinase promoter of the herpes simplex virus.

14. A murine myeloma cell according to claim 3.

15. A murine myeloma cell according to claim 6.

16. A murine myeloma cell according to claim 7.

17. A murine myeloma cell according to claim 8.

18. A method of producing non-immunoglobulin proteins comprising:
   (a) providing a clone of myeloma cells according to claim 1 stably transformed by said doubly-stranded DNA molecule;
   (b) growing said clone under conditions whereby said non-immunoglobulin protein is expressed; and
   (c) recovering said non-immunoglobulin protein thereby produced.

19. A method of producing non-immunoglobulin proteins comprising:
   (a) providing a clone of myeloma cells according to claim 2 stably transformed by said double-stranded DNA molecule;
   (b) growing said clone under conditions whereby said non-immunoglobulin protein is expressed; and
   (c) recovering said non-immunoglobulin protein thereby produced.

20. A method of producing non-immunoglobulin proteins comprising:
   (a) providing a clone of myeloma cells according to claim 3 stably transformed by said double-stranded DNA molecule;
   (b) growing said clone under conditions whereby said non-immunoglobulin protein is expressed; and
   (c) recovering said non-immunoglobulin protein thereby produced.

21. A method of producing non-immunoglobulin proteins comprising:
   (a) providing a clone of myeloma cells according to claim 17 stably transformed by said double-stranded DNA molecule;
   (b) growing said clone under conditions whereby said non-immunoglobulin protein is expressed; and
   (c) recovering said non-immunoglobulin protein thereby produced.

22. A method of producing non-immunoglobulin proteins comprising:
   (a) providing a clone of myeloma cells according to claim 13 stably transformed by said double-stranded DNA molecule;
   (b) growing said clone under conditions whereby said non-immunoglobulin protein is expressed; and
   (c) recovering said non-immunoglobulin protein thereby produced.

23. A method of producing non-immunoglobulin proteins comprising:
   (a) providing a clone of myeloma cells according to claim 14 stably transformed by said double-stranded DNA molecule;
   (b) growing said clone under conditions whereby said non-immunoglobulin protein is expressed; and (c) recovering said non-immunoglobulin protein thereby produced.

24. A method of producing non-immunoglobulin proteins comprising:
   (a) providing a clone of myeloma cells according to claim 15 stably transformed by said double-stranded DNA molecule;
   (b) growing said clone under conditions whereby said non-immunoglobulin protein is expressed; and
   (c) recovering said non-immunoglobulin protein thereby produced.

25. A double-stranded DNA molecule containing a coding sequence expressable in a myeloma cell comprising:
   (i) a coding sequence encoding a non-immunoglobulin protein and bounded by a translation start codon at its 5' terminus and a translation stop codon on its 3' terminus;
   (ii) a non-immunoglobulin promoter sequence adjacent to the 5' terminus of said coding sequence, said promoter sequence containing a transcription initiation site and capable of initiating transcription of said coding sequence in a mammalian myeloma cell;
   (iii) the 8-base pair nucleotide sequence 5'-ATTTGCAT-3' on the nontranscribed strand located 5' to the transcription initiation site of said promoter sequence and in a position whereby the rate of transcription of said coding sequence in a mammalian myeloma cell is increased; and
   (iv) a transcription enhancer element of a mammalian kappa light-chain immunoglobulin gene located so as to increase the rate of transcription of said coding sequence in a mammalian myeloma cell.

26. The DNA molecule of claim 25 wherein said immunoglobulin gene enhancer is a murine enhancer.

27. The DNA sequence of claim 25 wherein said promoter sequence is substantially homologous to the wild-type thymidine kinase promoter of the herpes simplex virus.

28. The DNA sequence of claim 26 wherein said promoter sequence is substantially homologous to the wild-type thymidine kinase promoter of the herpes simplex virus.

* * * * *